United States Patent [19]
Dosmann

[11] Patent Number: 5,305,093
[45] Date of Patent: Apr. 19, 1994

[54] SPECTROMETER FOR CONDUCTING TURBIDIMETRIC AND COLORMETRIC MEASUREMENTS

[75] Inventor: Andrew J. Dosmann, Mishawaka, Ind.

[73] Assignee: Miles Inc., Elkhart, Ind.

[21] Appl. No.: 785,987

[22] Filed: Oct. 31, 1991

[51] Int. Cl.$^5$ .................. G01N 21/00; G01N 21/27
[52] U.S. Cl. ................. 356/435; 356/414; 250/575
[58] Field of Search ............ 356/414, 334, 320, 319, 356/435, 411, 565; 250/574, 575, 576

[56] References Cited

U.S. PATENT DOCUMENTS

| | | |
|---|---|---|
| 4,042,304 | 8/1977 | Martin et al. ................ 250/574 |
| 4,171,909 | 10/1979 | Kramer et al. ................ 356/435 |
| 4,678,325 | 7/1987 | Lehtikoski et al. ............ 356/334 X |

OTHER PUBLICATIONS

"HbAlc ASAP", DCA 2000 Analyzer pp. 1–4, 1989.
Korn et al., "Double Beam Vacuum Ultraviolet Spectrometer and Logarithmic Radiometer," Applied Optics, vol. 111, #3, pp. 517–520.

Primary Examiner—Vincent P. McGraw
Assistant Examiner—K. P. Hantis

[57] ABSTRACT

A dual beam spectrometer for conducting both turbidimetric and colormetric measurements includes a housing with a light source. The housing further includes source exit apertures that form light from the light source into a sample light beam and reference light beam. A sample cartridge for containing sample material to be measured is mounted in the housing in the path of the sample light beam. The spectrometer also includes a detector assembly for detecting the sample light beam and the reference light beam. The detector assembly includes a first detector that senses or detects sample light beam and a second detector that senses or detects the reference light beam. A sample light beam detection aperture tube is positioned in the housing between the sample cartridge and the first detector. Similarly, a reference light beam detection aperture tube is positioned between the sample cartridge and the second detector.

3 Claims, 1 Drawing Sheet

SPECTROMETER FOR CONDUCTING TURBIDIMETRIC AND COLORMETRIC MEASUREMENTS

BACKGROUND OF THE INVENTION

A. Field of the Invention

The present invention relates generally to a new and improved spectrometer; and more specifically, to a new and improved spectrometer capable of conducting both turbidimetric and colormetric measurements.

B. Description of the Prior Art

Regular transmission optics are most commonly used for colormetric measurements, while diffuse transmission optics are commonly used for turbidimetric measurements. Due to these different optics, a single spectrometer cannot perform both colormetric and turbidimetric measurements. Moreover, if conventional regular transmission optics are used to perform turbidimetric sample measurements, accuracy problems occur. These accuracy problems manifest themselves in a large instrument to instrument bias due to opto-mechanical variations between instruments. Conventional optics typically eliminate inaccuracy by calibration of each instrument using samples of known turbidity. A correlation between the known levels and the instrument lends results in a calibration curve that is used to correct for bias. Another method of removing the inaccuracy is to precisely align each optical system in the manufacturing process to eliminate the opto-mechanical variations. While both methods of correction are viable, neither is an acceptable procedure when manufacturing a large number of instruments.

Several systems are known in the prior art; however, none of these systems includes a dual beam spectrometer that can perform both turbidimetric and colormetric analysis. For example, U.S. Pat. No. 4,457,893, discloses a system that measures light absorption of a liquid medium with an antibody before and after agglutination reaction by using a wavelength of light which is absorbable by the antibody. This system, however, can perform only colormetric measurements of the agglutination reaction. Another system is disclosed in Japanese Patent 1,112,162. This system includes two photometric systems used to perform both regular and diffuse transmission measurements of agglutinated samples. Again, two systems are necessary. Japanese Patent No. 63/191,962 discloses a system or instrument that automatically performs immunoassays making use of a latex agglutination reaction. U.S. Pat. No. 4,766,083 discloses a system that uses a laser for a light source to detect diffuse transmission. A laser is not necessary in the present invention. U.S. Pat. No. 4,429,040 discloses an assay that is used for detection and determination of fibrin monomer in blood plasma. British Patent No. 1,598,129 discloses a system or an instrument that automatically performs immunoassays using a latex agglutination reaction.

In Soviet Union Patent No. 1186958, there is disclosed a system of calibration for a regular transmission photometer. A patent for an optical sample cell is disclosed in Soviet Union Patent No. 883714. Similarly, a calibration procedure for a regular transmission spectrometer correction filter is described in Soviet Union Patent No. 1153240. U.S. Pat. No. 3,436,187 discloses a method of estimating turbidity employing polystryrene latex suspensions as samples. Also, U.S. Pat. No. 4,495,293 discloses a fluorometric assay of ligands by a reaction with a reagent which alters emission properties of a fluorescer.

SUMMARY OF THE INVENTION

Briefly, the present invention is directed to a new and improved dual beam spectrometer capable of conducting both turbidimetric and colormetric measurements with the same optical system. The spectrometer includes a housing with a single light source mounted in the housing. Spaced from the light source are source exit apertures fabricated in the housing and positioned to form light emanating from the light source into a sample light beam and a reference light beam. A sample cartridge for containing a sample is mounted in the housing in the path of the sample light beam and spaced from the path of the reference light beam.

The spectrometer further includes a detector or detection assembly for detecting the sample light beam and the reference light beam. The detection assembly includes a first detector and a second detector. The first detector is positioned to detect the sample light beam. A sample light beam detection aperture tube is mounted in the housing between the sample cartridge and the first detector. Similarly, the second detector is positioned to detect the reference light beam, and a reference light beam detection aperture tube is mounted in the housing between the sample cartridge and the second detector. The detection aperture tubes decrease the sensitivity of the first and second detectors to the diffuse component of light, thus increasing the resolution between highly agglutinated latex samples.

BRIEF DESCRIPTION OF THE DRAWING

The above and other objects and advantages and novel features of the present invention will become apparent from the following detailed description of a preferred embodiment of the invention illustrated in the accompanying drawing wherein.

Figure 1:
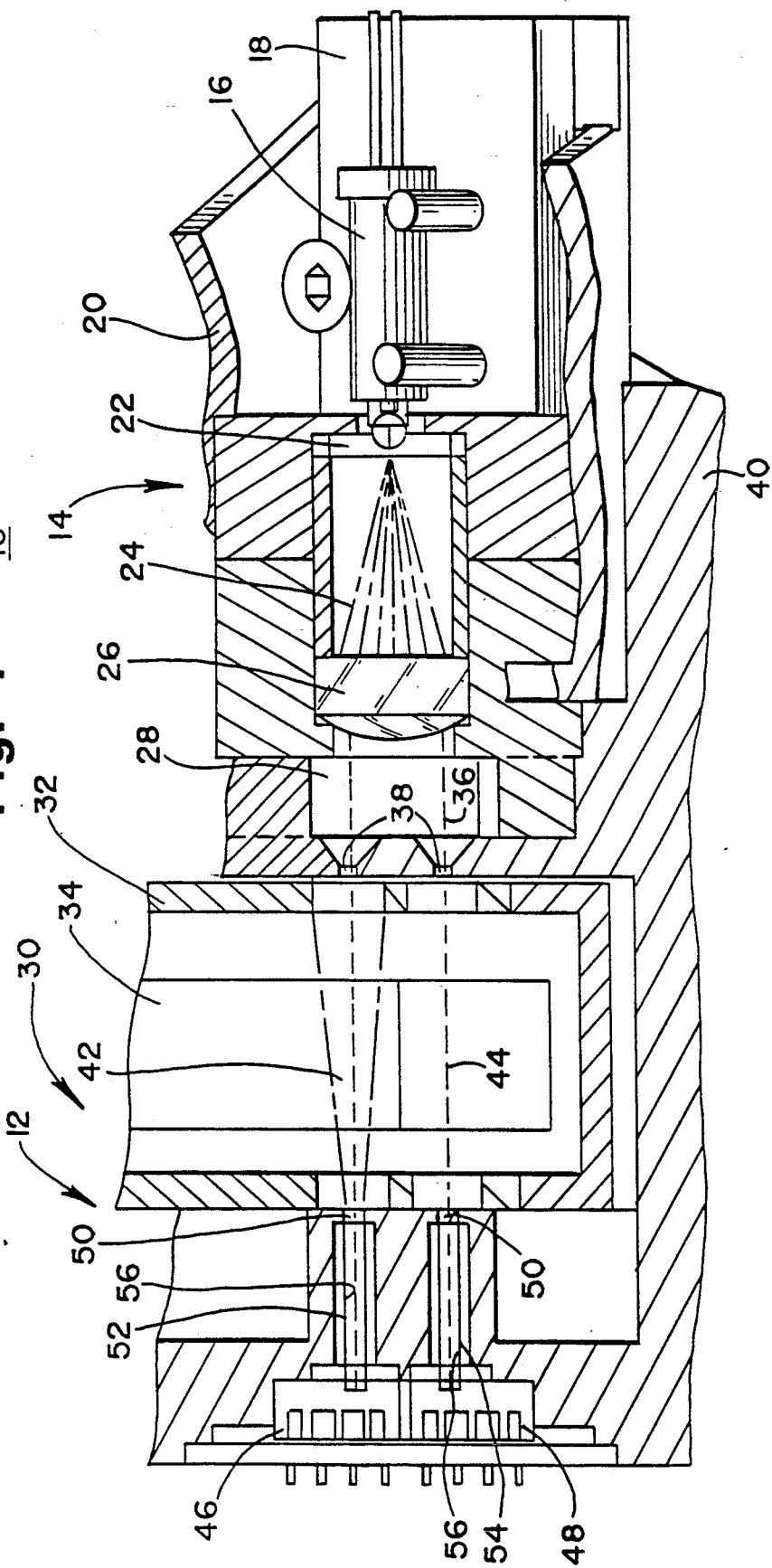
FIG. 1 is a vertical side, partially cut-away view of the source optics and detector optics of a spectrometer constructed in accordance with the principles of the present invention.

The invention is susceptible to various modifications and alternative forms, and it should be understood that it is not intended to limit the invention to any particular form disclosed. On the contrary, the intention is to cover all modifications, equivalents, and alternatives falling within the spirit and scope of the invention as defined by the appended claims.

DESCRIPTION OF THE PREFERRED EMBODIMENT

Referring to FIG. 1, there is illustrated a dual beam spectrometer generally designated by the reference numeral 10. The spectrometer 10 performs high accuracy regular transmission turbidimetric measurements and high accuracy colormetric measurements using the same optical system. The spectrometer 10 can be of the type used in an instrument that performs hemoglobin $A1_c$ assays.

The spectrometer 10 provides highly accurate turbidimetric measurements and colormetric measurements without calibration or special opto-mechanical alignments. Moreover, the spectrometer 10 can achieve a between instrument coefficient of variation of less than 1.5% for turbidimetric measurements within a range of 1.0000T to 0.0100T (transmission). The spectrometer 10 is a factor greater than four times more accurate than many known research spectrometers. The high accuracy of the spectrometer 10 is accomplished by a design that controls light beam collimation and opto-mechanical alignment between a light source, a sample and detection optics.

Known regular transmission spectrometers have poor transmission resolution between samples that scatter a large portion of incident flux. This poor transmission resolution is due to the lack of detection optics designed to reject the diffuse component caused by light scattering within a turbid sample. The spectrometer 10 of the present invention, however, improves transmission resolution with detector or detection optics generally designated by the numeral 12 that reject the diffuse component resulting in increased accuracy when measuring samples with a high amount of turbidity. The detection optics 12 are designed to increase sensitivity to the regular transmittance component of light while decreasing sensitivity to the diffuse or scatter component of light. This increase in sensitivity and thus resolution contributes to improved accuracy in measuring highly turbid samples thereby eliminating the need for special calibrations or special opto-mechanical alignments in the manufacturing process. Since accurate turbidimetric measurements can be performed with the regular transmission optics of the spectrometer 10, colormetric measurements are also easily performed with the same optics.

In addition to the detection optics 12 of the spectrometer 10, there are two other features of the optical design that contribute to maintaining a high degree of accuracy when performing turbidimetric measurements of highly agglutinated polystyrene particles having diameters of 70 to 110 uM (micrometers). One of these features is the source optics generally designated by the reference numeral 14. The source optics 14 includes a lamp 16 which is a halogen light source mounted in a lamp holder 18. The halogen lamp 16 has a frosted flame formed lens. The frost breaks up the image of the filament while still allowing the output to be condensed by the lens. In addition, the alignment of the output of the lamp is held to within $\pm 5°$ with respect to the mechanical base of the lamp. The combination of the lamp features results in a 40% signal throughput differential between the sample to reference channels, as compared to a 95% throughput differential without the lamp features. The decrease in throughput differential eliminates the need for lamp alignment during the manufacturing process of the instrument. A collimation spatial filter 22 is mounted adjacent to the lamp 16 to filter the light emanating from the lamp 16. A filtered beam of light 24 impinges on and passes through a collimation lens 26 also mounted in the housing 20. This beam of light 24 is directed onto a spectral bandpass filter 28. The lamp 16, the spatial filter 22 and the collimating lens 26 form a simple optical collimator that colliminates light before it enters the bandpass filter 28. The amount of collimation can be measured by calculating the percentage increase in light beam diameter compared to the nominal or perfect collimated beam diameter at a detector plane. The collimation is directly proportional to the diameter of the collimation spatial filter 22. As the diameter of the filter 22 increases, beam collimation degrades at the detector optics 12, but the signal level increases.

The nominal collimation which would provide the highest signal throughput for the spectrometer 10 was determined by characterizing the effect of collimation on system performance. Hemoglobin and agglutinated latex sample absorbance versus collimation were measured with collimation spatial filters having diameters from 0.010 inch to 0.050 inch (0.025 to 0.13 cm). It was determined that for blank corrected hemoglobin samples absorbance was not sensitive to collimation, while the absorbance of the agglutinated latex was only sensitive to collimation when the filter diameter exceeded 0.030 inch (0.076 cm). A collimation limit of 34% was established to provide the highest single throughput without any compromise to system accuracy. All mechanical tolerances that directly affected collimation were characterized with several mechanical tolerance studies. The mechanical tolerances that were given to each component were then assigned so that no one tolerance or combination of tolerances could cause a beam divergence of greater than 34%. The accuracy error for turbidimetric measurements caused by mechanical tolerances within the housing 20 of the spectrometer 10 were effectively reduced to zero by maintaining a specific degree of collimation.

The third feature of the spectrometer 10 is the sample area generally designated by the reference numeral 30. The sample area 30 includes a cartridge holder 32 mounted in the spectrometer housing 20 and a sample cartridge 34 that is positioned in the cartridge holder 32 and holds a sample to be measured. An important feature of the present invention is the opto-mechanical alignment of the source optics 14, the sample area 30 and the detection optics 12. In the preferred embodiment, a monochromatic beam 36 of 531 nm (nanometers) passes into source exit apertures 38 formed within an optics holder 40. The source exit apertures 38 form the monochromatic beam of light 36 into a sample light beam 42 and a reference light beam 44. In this arrangement the sample light beam 42 passes through a sample contained in the sample cartridge 34 and the reference beam 44 passes under the sample cartridge 34 through air.

The sample beam 42 is detected by a first detector/amplifier 46 and the reference beam 44 is detected by a second detector/amplifier 48. These detectors 46 and 48 may be any photodetector such as the Texas Instrument photodetector designated by part no. 28934P. The first detector 46 is mounted within the optics holder 40 in a position perpendicular to the sample light beam 42. Similarly, the second detector 48 is mounted in the optics holder 40 in a position perpendicular to the reference light beam 44. To reach the first detector 46, the sample light beam 42 passes through a detection aperture 50. The reference beam 44 also reaches the second detector 48 through detection aperture 50. To minimize accuracy errors, the mechanical alignment between the source exit apertures 38 and the detection apertures 50 must be held to a close tolerance. This can be accomplished through the unibody molded optics holder 40 which contains both the source exit apertures 38 and the detection apertures 50. The alignment of these apertures 38 and 50 is held fixed to within the required tolerance through a molding process in forming the unibody optics holder 40. Although turbidimetric accuracy errors increase exponentially with mechanical misalignment between the light source 16, the sample cartridge 34, and the light detection optics 12, these accuracy errors are limited to less than 1% by the unibody molded optics holder 40 which contains the light source 16 and the detection optics 12. The unibody construction of the optics holder 40 maintains the source exit apertures 38 and the detection apertures 50 in fixed relationship. These are held fixed to within the required mechanical tolerance through the molding process, thus minimizing the mechanical tolerances that affect the alignment between these two optical assemblies.

Regular transmission spectrometers generally have poor transmission resolution between samples of high turbidity because they detect a significant amount of scattered or diffused transmission. The dual beam spectrometer 10 increases the resolution between highly agglutinated latex samples by decreasing the sensitivity of the detection optics to the diffuse component through the employment of a sample light beam detection aperture tube 52 and a reference beam detection aperture tube 54. The detection aperture tubes 52 and 54 can be black ABS tubes that are mounted in the optics holder 40 between the sample cartridge 34 and the detectors 46 and 48, respectively. Each of the detection aperture tubes 52 and 54 has a length of 0.600 inch (1.52 cm) with 4/40 internal threaded black walls. The inside diameter of each of the tubes 52 and 54 is 0.065 inch (0.165 cm). The threads 56 baffle a majority of the off axes light (diffuse component) that is present when measuring turbid samples. The serration can be in the form of threads 56.

The combination of the length and diameter of the detection aperture tubes 52 and 54 results in a detector viewing area that is limited to the sample area. Scattered light entering the tubes 52 and 54 from angles exceeding 5° is prevented from passing down tubes 52 and 54 to the respective detectors 46 and 48. The resulting increase in relative absorbance of highly agglutinated samples provides increased absorbance resolution which is a contributing factor to the improved accuracy of the spectrometer 10.

The dual beam spectrometer 10 provides high accuracy regular transmission measurements of turbid samples without special calibrations or tedious optical alignments during the manufacturing process. Since turbidimetric measurements are done with regular transmission optics, colormetric measurements are easily performed by the spectrometer 10 with the same optics.

I claim:

1. A dual beam spectrophotometer for conducting turbidimetric and colorimetric measurements having dual apertures for forming a monochromatic beam of light into a sample light beam and a reference light beam and a detector assembly for separately detecting the sample light beam and the reference light beam; said dual beam spectrometer having aperture tubes for transmitting the sample light beam after the sample light beam passes through a sample and the reference light beam after the reference light beam passes through air, respectively, directly to the detector assembly; said aperture tubes consisting essentially of tubes having an inside diameter of about 0.065 inch and a length of about 0.6 inch wherein light entering said tubes from angles exceeding 5 degrees is prevented from passing down the tubes to said detector assembly.

2. The dual beam spectrophotometer of claim 1 in which the tubes further contain internal serration.

3. The dual beam spectrophotometer of claim 2 in which the serration is in the form of 4/40 black threads.

* * * * *